US006270345B1

(12) United States Patent
Abbott et al.

(10) Patent No.: US 6,270,345 B1
(45) Date of Patent: Aug. 7, 2001

(54) VANE MOTOR FOR DENTAL AND MEDICAL HANDPIECES

(75) Inventors: John D. Abbott, deceased, late of Redwood City, by Beth Ann Abbott, executor; Arthur Vassiliadis, Dana Point, both of CA (US)

(73) Assignee: Dove Systems, Inc., Redwood City, CA (US)

( * ) Notice: Subject to any disclaimer, the term of this patent is extended or adjusted under 35 U.S.C. 154(b) by 0 days.

(21) Appl. No.: 09/429,777

(22) Filed: Oct. 28, 1999

(51) Int. Cl.[7] .................................................. A61C 1/05
(52) U.S. Cl. .................................................. 433/132
(58) Field of Search ............................................. 433/132

(56) References Cited

U.S. PATENT DOCUMENTS

| 4,225,308 | * | 9/1980 | Lohn ..................................... 433/132 |
| 5,423,678 | * | 6/1995 | Nakanishi ......................... 433/132 X |
| 5,797,743 | * | 8/1998 | Bailey ............................... 433/132 X |

* cited by examiner

Primary Examiner—Nicholas D. Lucchesi
(74) Attorney, Agent, or Firm—Jeffrey Slusher

(57) ABSTRACT

An arrangement for driving a rotary dental or medical tool attached to a handpiece includes a vane motor that is compact enough to be mounted within the head of the handpiece. The vane motor includes a rotor, which is mounted within an eccentric bore of a cylinder, which forms a stator. Inlet ports into the vane motor preferably open perpendicular to the rotor's axis of rotation so that intake air is directed substantially directly at the vanes. An arrangement of the inlet and of outlet ports allows a duty stroke for each vane up to 240 degrees. Inlet and exhaust air preferably enters and exits the vane motor via annular channels surrounding either end of the cylinder. There is then no need to align the motor angularly when it is installed in the head. A radial gap is preferably provided between the rotor and the shaft it is mounted on. Channels connecting the bottom of each vane slot with this gap reduce the vacuum effect acting on the vanes as they extend. The rotor can preferably also move a small longitudinal distance of the shaft so that it can find its own balance position. The speed of the vane motor can be varied using a user-controller pressure controller.

12 Claims, 14 Drawing Sheets

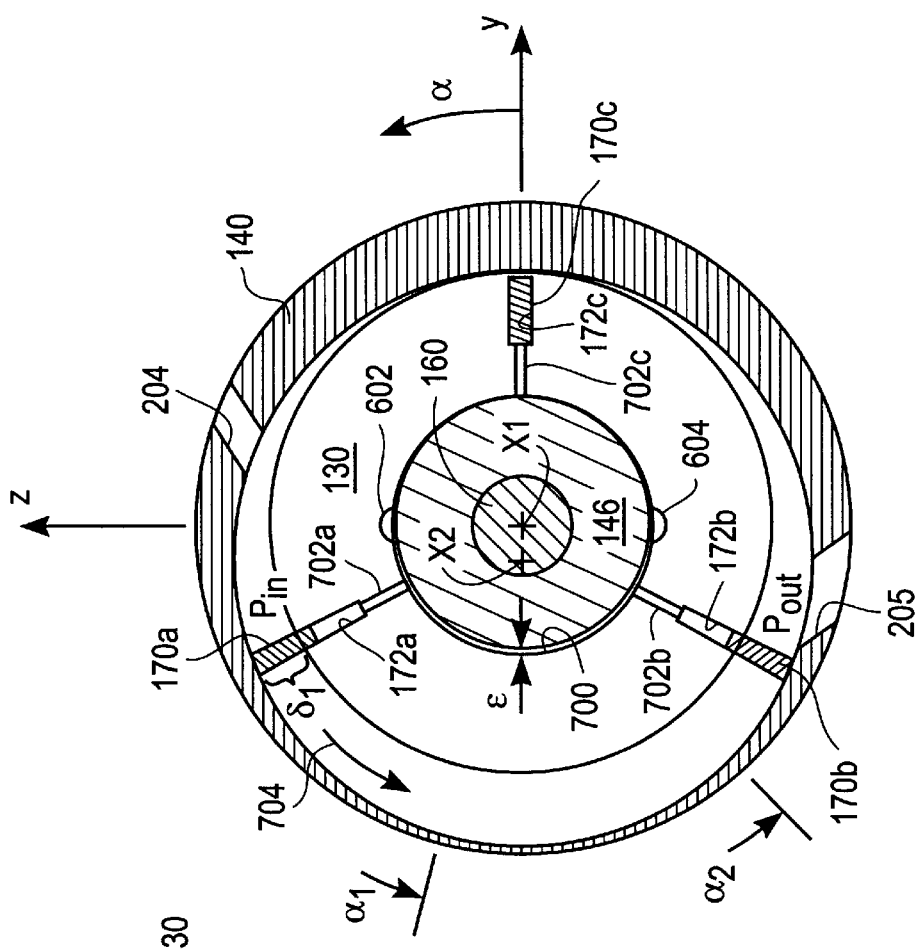
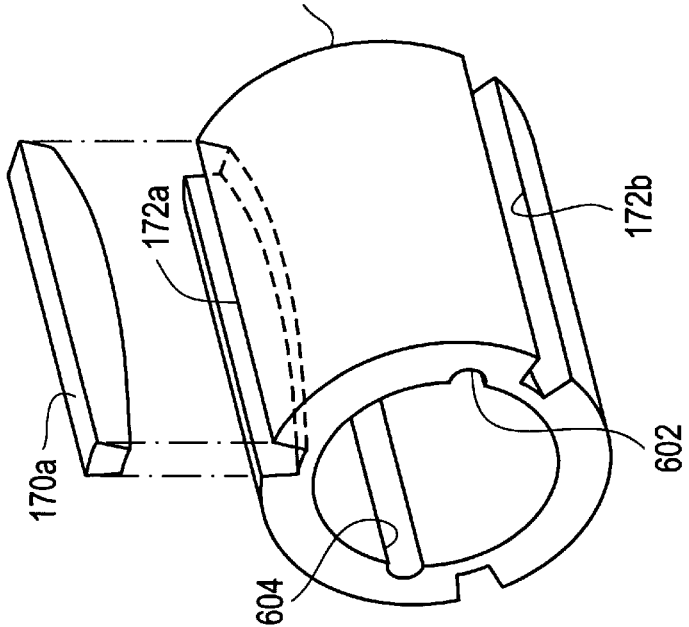

VANE MOTOR FOR DENTAL AND MEDICAL HANDPIECES

BACKGROUND OF THE INVENTION

1. Field of the Invention

This invention relates to a vane motor for use in dental and medical handpieces.

2. Background Art

The common dental handpiece is familiar—sometimes painfully so—to almost everyone who has ever been to a dentist. These handpieces usually include a pneumatic, rotary motor that drives some tool such as a drill bit or burr to allow the dentist to drill into or reduce a tooth. Similar devices also find use in medical contexts, such when drilling into or reducing bone, for example, in order to prepare a proper surface for attaching artificial joint members, for inserting anchoring pins, and so on.

One design goal for most handpieces is that their motors should be able to develop enough torque to drive the tool at a high enough rate of rotation, even under load. In one common type of handpiece, a turbine is mounted on a rotating shaft within the head of the handpiece. A disadvantage of an air-driven turbine is that its torque output is relatively low. Moreover, not only do turbines have a no-load speed that is needlessly high, but their speed also drops drastically when loaded.

Another common type of air-driven motor uses vanes instead of a turbine. In these devices, mainly flat, radial vanes are mounted to extend outward from a rotating shaft in planes that intersect the axis of rotation of the shaft. These vane motors in general deliver more torque than turbines, especially at the low rpm's normally preferred for cutting, but they typically have a much more complicated structure than turbines. For example, the rotating shaft on which the vanes are mounted is typically is mounted eccentrically, which means that the vanes must be able to move radially in the shaft as they turn. Many vane motors then require springs or other arrangements to ensure that the vanes extend fully where they are supposed to. This leads to other problems, such as the need to reduce friction between the vanes and the motor housing without losing power because of gaps.

Another goal is that the handpiece should not be too bulky or heavy. Here, the extra structures normally required in a vane motor work to particular disadvantage. One solution, both with turbine and vane motors, has been to mount the motor in the handle of the handpiece. A transmission system must, however, then be included from the motor to the head of the handpiece in order to drive the shaft on which the cutting or drilling tool is mounted. This transmission of course leads in turn to even more weight and bulk, and to reduced power.

In order to fit the motor in the tight space available in a dental or medical handpiece, the air intake and outlet ports must often be arranged in way that reduces the force the air can apply to the vanes, or that reduces the duty stroke of the vanes, or both. These port arrangements are, moreover, typically open into the end of the motor housing, that is, such that the intake air is directed along the vanes, not directly against them. Not only does this reduce the force of the air on the vanes, but it also mean that the motor housing itself must be precisely keyed so that the ports are properly aligned when the housing is installed into its opening in the handpiece.

The two main goals—high torque and compactness—typically conflict. One could, for example, increase the size of the air motor, but if the handpiece then becomes too heavy for the dentist to hold comfortably for the time it takes, for example, to do a tooth reduction, then achieving the extra power will not have been worth the effort.

Sometimes, vane motors require structures that make it harder for them to meet both design goals. In some known vane motors, for example, separate cylindrical members are included between the vanes and the inner wall of the handpiece housing, in order to reduce friction and wear on the vanes. In some cases, the outer tips of the vanes are keyed into this cylinder so that the cylinder rotates along with the vanes. This added part not only increases bulk and weight, and thus puts more stress on bearings. Furthermore, by increasing the inertia of the rotating parts of the motor, it reduces the power available for cutting.

Because of the extra complexity and weight of known vane motors, no vane motors now in use in dental or medical handpieces are even able to include the motors within the head of the handpiece. In other words, it has not been possible to make use of the high torque available from vane motors in a device that is compact and comfortable enough for dentists and surgeons to actually want to use in practice.

Still another problem common in existing motors is that they are not self-starting. This is generally a result of the other shortcomings of conventional motors—friction, inertia, inefficient porting, and so on. Whatever the cause, however, the solution is the same: yet another structure must be built in to start the motor. This of course simply makes the problem of excess bulk and complication even worse.

There are many known devices that attempt to achieve one or the other of these goals, or to find some suitable compromise. Representative conventional pneumatic motors used in dental handpieces are described in, for example, the following U.S. patents:

U.S. Pat. No. 4,120,623 (Lohn, Oct. 17, 1978);

U.S. Pat. No. 4,175,393 (Frank, Nov. 27, 1979);

U.S. Pat. No. 4,177,024 (Löhn, Dec. 4, 1979);

U.S. Pat. No. 4,225,308 (Lohn, Sep. 30, 1980);

U.S. Pat. No. 4,278,427 (Lingenhöle, et al., Jul. 14, 1981);

U.S. Pat. No. 4,403,958 (Löhn, Sep. 13, 1983);

U.S. Pat. No. 4,740,144 (Biek, Apr. 26, 1988); and

U.S. Pat. No. 5,064,361 (Kristof, et al., Nov. 12, 1991).

These known devices all suffer to some extent from insufficient torque or bulkiness, or from any of the several other problems associated with vane motors mentioned above. What is needed is a motor for dental and medical handpieces that doesn't, or at least not to the same extent.

SUMMARY OF THE INVENTION

The invention provides an arrangement for driving a rotary dental or medical tool that comprises a source of pressurized gas; a handpiece that includes a handle and a head, which is attached to the handle; a rotary vane motor, to which the tool is attached; and an inlet conduit (such as a channel through the handle) leading the pressurized gas to the vane motor. The vane motor is so compact that it may be mounted within the head of the handpiece.

The vane motor according to the invention includes a cylindrical rotor and a cylindrical stator with an eccentric, cylindrical, longitudinally extending bore. The rotor is mounted within this eccentric bore, but with the rotor and stator concentric about a longitudinal axis, which is the axis of rotation of the rotor. A plurality of vanes are mounted in corresponding, substantially lengthwise-extending slots formed in the rotor. The vanes are movable in their respective slots in a radial direction that is perpendicular to the axis of rotation. An inlet port and an outlet port are formed as openings through the stator. Either the inlet or the outlet port, or both, preferably includes a plurality of openings.

In the preferred embodiment of the invention, the inlet port is formed as one or more bores that extend mainly in a plane that is perpendicular to the axis of rotation of the rotor. Inlet gas entering through the inlet port is then directed substantially directly against the vanes and outer surface of the rotor, thereby directly imparting momentum in a tangential direction of rotation.

The vanes have a uniform relative angular separation of $\sigma=360/n$ degrees, where n is the number of vanes. The inlet port is preferably located within $\sigma$ degrees from an angular zero position, which is defined by a line that extends perpendicularly from the axis of rotation through a closest point between the outer surface of the rotor and the inner surface of the eccentric cylinder. The outlet port is then preferably located at least $\sigma$ degrees away from the inlet port and $\sigma/2$ beyond an angular position 180 degrees away from the angular zero position, measured in the direction of rotation of the rotor.

Multiple inlet ports can be used, with benefit, at locations both before and after the single port location; inlet ports are preferably located beyond the zero position but no later than $\sigma/2$ degrees before the 180 degree position. Multiple outlet ports can be used at locations after the single outlet port location but earlier than $\sigma$ degrees before the first outlet port.

An annular inlet channel is preferably located between the stator and the head and connects the inlet port via the inlet conduit with the source of pressurized gas. Similarly, an annular outlet channel is preferably located between the stator and the head and connects the outlet port via an outlet conduit (such as an exhaust channel in the handle) with the ambient environment. This makes the communication of pressurized gas with the inlet port and of exhaust gas from the vane motor with the ambient environment independent of the angular alignment of the vane motor within the head of the handpiece.

The rotor is mounted on a shaft. There is preferably a radial gap between the rotor and the shaft and a keying arrangement that rotationally secures the rotor to the shaft. A channel is preferably provided to connect an inner portion of each slot with the radial gap. These channels, together with the gap, form means for reducing any vacuum formed under each vane as it extends in its slot.

The keying arrangement preferably allows slight movement of the rotor in the longitudinal direction on the shaft. Rotor end caps are then preferably provided to restrain movement of the rotor on the shaft. There is preferably a longitudinal gap between the rotor and the end caps so that the rotor can "float" longitudinally on the shaft and assume a balanced position when rotating.

The shaft and the rotor share a common axis of rotation, The dental or medical tool is preferably securely attached to the shaft, so that the axis of rotation of the rotor is also the axis of rotation of the tool. Thus, the vane motor preferably drives the tool directly.

The invention preferably also includes a supply air controller that allows the user to vary the amount of pressurized gas delivered to the vane motor and thereby to control the rotational speed of the vane motor and the tool.

BRIEF DESCRIPTION OF THE DRAWINGS

FIG. 6 is a perspective view of the rotor and of one of the vanes.

FIG. 7 is a simplified cross-sectional end view of the rotor within the eccentric cylinder.

DETAILED DESCRIPTION

Figure 1:
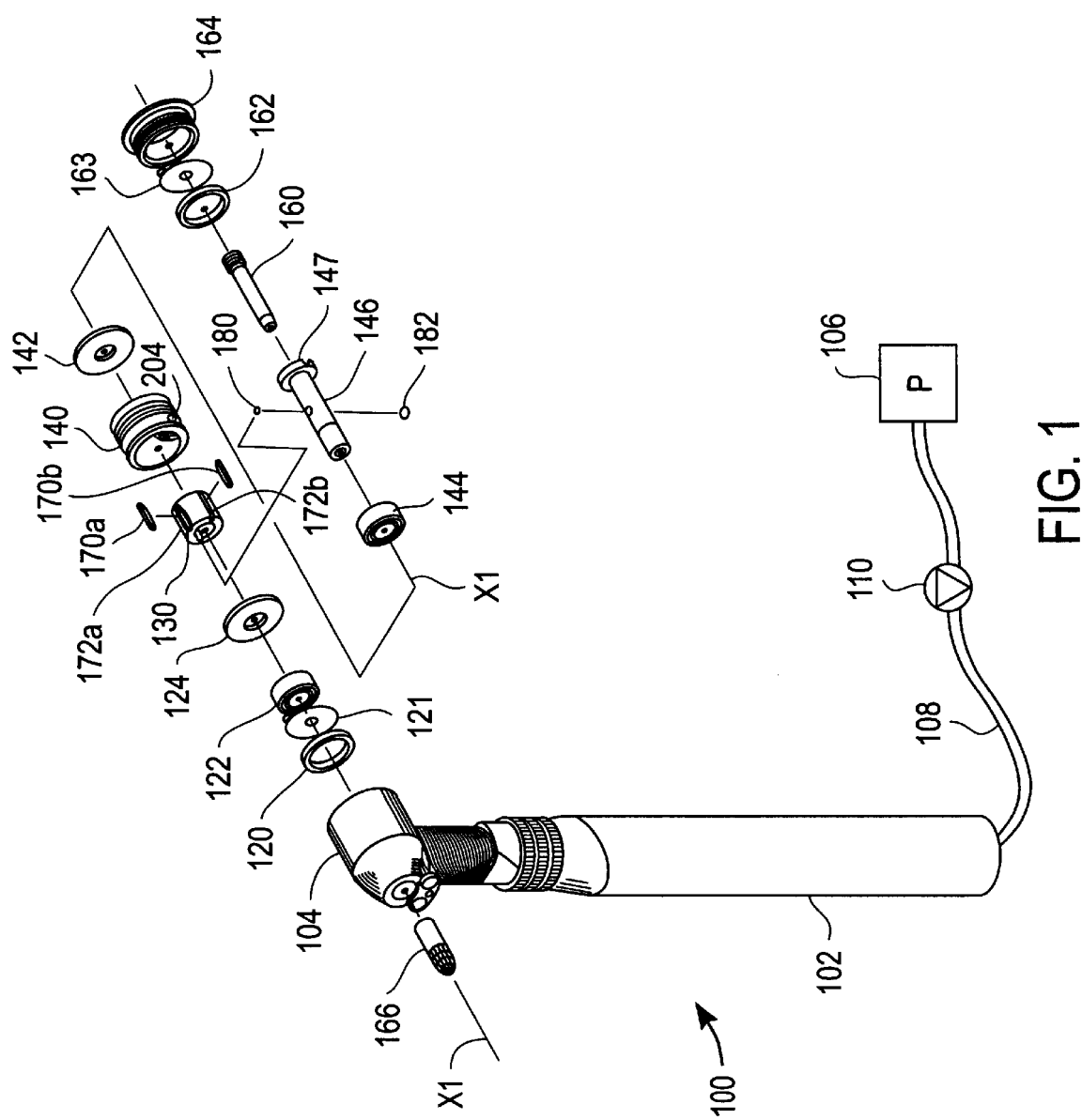
FIG. 1 shows the main components of the dental or medical handpiece according to the invention.

FIG. 1 shows the main components of a system for driving a rotating dental or medical device for abrading or cutting hard body structures such as tooth or bone. A dental handpiece is indicated generally by reference number 100. The handpiece includes a handle 102 (shown shortened) and a head 104, which forms a housing for the motor used to drive the tool. The motor according to the invention is described in detail below. One advantage of the invention that can be seen even at this early point, however, is that the motor according to the invention is compact enough to fit completely within a standard handpiece head.

Pressurized gas, usually air, is delivered from a conventional pressure source 106 to the handpiece via standard tubing 108 and some form of regulator or controller 110, that controls the flow of air to the handpiece and thus the speed of the motor. The regulator 110 is usually a foot switch or, occasionally, a button or switch in the handle 102 of the handpiece itself, which controls a pinch or needle valve. The regulator is particularly useful with this invention, since the motor according to the invention not only delivers useful torque at low rpm's, at which cutting is most efficient, but also allows for torque delivery at variable speeds.

The handpiece 100 also includes conventional tubes or channels to lead the pressurized gas to inlet ports or channels in the head 104 and thus to inlet ports to the motor. This arrangement is generally well known, and is used to control even existing dental drills; it is therefore not described in greater detail here. The invention is not dependent on how the pressurized gas is supplied to the handpiece, or how the gas is channeled to the head. The porting arrangement leading the gas from the head to the motor itself is, however, novel and is used to particular advantage in this invention.

The head 104 also forms a housing for the motor. This housing may be manufactured in any known manner to have a cylindrical interior wall, with cylindrical recesses as necessary in which the various annular parts of the motor seat when mounted.

In the preferred embodiment of the invention, the motor includes the following parts, which are assembled concentric with a central assembly axis X1, which is also the axis of rotation of the motor. An O-ring 120 is preferably mounted innermost in the head 104. In order to increase its ability to seal against supply air leakage, even when the air is under pressure, the O-ring is preferably a square O-ring, that is, a radial cross-section is essentially rectangular rather than circular. Proceeding outward along the central mounting axis is an inner wave washer 121, an inner bearing 122, an inner cylinder cap 124, a rotor 130, which fits within an eccentric cylinder 140, an outer cylinder cap 142, and outer bearing 144, a spindle 146, a collet 160, an outer O-ring 162, an outer wave washer 163, and an end cap 164. The wave washers are included as one way to pre-load the bearings 122, 144; any other known means of pre-loading the bearings may, of course, be used instead.

The outer surface of the cylinder 140 preferably has threading that mates with internal threading in the head 104. The end cap 164 preferably has similar threading. The motor can thus be easily assembled and installed in the head simply by installing the various parts in their respective recesses in the head, then screwing in the cylinder 140, with the rotor and vanes in place within it, and then screwing in the end cap 164.

The spindle 146 preferably has a head 147 at the outer end to form one wall or flange against which the outer surface of the outer bearing 144 rests when the motor is assembled and installed. The inner end of the spindle 146 is secured conventionally in the inner race member of the bearing 122. The washer 121 forms the inner retaining surface for the inner bearing 122. The spindle, and thus the rotor 130, can therefore rotate freely supported by the bearings 122, 142. The bearings may be chosen using normal design methods and be of any conventional type. In one prototype of the invention, ball bearings were used.

Vanes 170*a*, 170*b* (only two are shown in FIG. 1) are mounted in corresponding, lengthwise extending (in the direction of the axis of rotation X1) slots 172*a*, 172*b*, in the outer surface of the rotor 130 with a tolerance that allows them to slide radially out and into the slots substantially freely, but not with such a gap that they wobble out of their respective radial planes and reduce their ability to seal against the inside surface of the cylinder 140. In order to maximize balance, the vanes are preferably arranged with uniform angular separation. Thus, in an n-vane motor, the vanes have an angular separation σ=360/n degrees.

One advantage of the invention can be realized even at this point—its simplicity. Disregarding the spindle and collet (which may be combined if desired), the three-vane embodiment of the vane motor according to the invention needs only nine parts: the cylinder 140, the rotor 130, three vanes, the two end caps 124, 142, and the bearings 122, 144.

The rotor may be securely mounted on the spindle in any known manner such as by simple press fitting. In the preferred embodiment of the invention, however, it is mounted using steel balls 180, 182, that act as keys that rest within mating indentations in the spindle, which forms the rotor shaft, and mating, lengthwise extending grooves in the inner surface of the rotor of the spindle 146. Balls are advantageous, since they are easy to install, requiring only simple indentations in the shaft, and they allow the rotor to "float" with minimum friction longitudinally on the shaft (see below for further explanation of this feature). Instead of balls, however, pins, ridges or some other protrusions could be provided on the shaft to mate with the grooves in the rotor; one could also have the protrusions or balls mounted in the rotor itself, with longitudinal grooves in the shaft.

The indentations and grooves are arranged with equal angular distance between them (in the case of two balls, the indentations are diametrically opposite each other) in their respective members so as to maintain balance. A small radial tolerance or gap, on the order of 0.025–0.051 mm (0.001–0.002 inches), is then created between the inner diameter of the rotor and the outer diameter of the spindle. This creates a floating armature for the rotor: The gap allows the rotor to "float" lengthwise on the spindle, to find its own balance position, and to seek its own clearance to the caps 124, 142. The gap between the ends of the rotor and the caps need not be large—in one prototype of the invention, the gap was only 0.0203 mm (0.0008 in.) and will in general be less than 0.0254 mm (0.001 in.) It also allows the bearings 122, 144 to be longitudinally fixed even though the rotor is allowed to move longitudinally, at least for a small distance between the caps 124, 142. This "floating" of the rotor, with torque transferred by the balls, also enables the invention to better handle lateral and radial loads on the spindle/shaft 146 (for example, as the tool is pressed against a tooth) without affecting clearances.

The motion of the rotor also creates an air bearing between it and the inner surfaces of the caps. This also makes it possible to avoid the splines, shimming and testing required in prior art designs. Torque is then transferred from the spindle to the rotor via the balls 180, 182.

The collet 160 may also be mounted within the spindle 146 in any known manner. In many applications, a simple press fit will suffice. In one prototype of the invention, the collet, at least at the inner end, was split and thus compressed when it was inserted into the bore of the spindle. It is also possible to mount the collet in the spindle using mating threads.

A tool 166 such as a burr is attached to the spindle 160, also in any known manner, through an opening in the innermost part of the head 104. The attachment should allow for easy changing and attachment of the tool. This is well known, however, and is therefore not described further here.

The bearings 122, 144 may be manufactured to include end walls that take the place of the end caps 124, 162. This would reduce the number of parts one would need to assemble into the head.

The materials used to manufacture the various parts of the motor according to the invention may be chosen and shaped using normal design and machining methods. In the prototype of the invention, the head 104 was machined from brass, as was the cap 164; the rotor 130 was of titanium; and the remaining metal parts were of stainless steel. Other metals may of course be used.

The vanes should be made of a synthetic material that is light, not for reasons stated above, but also to allow them to move quickly in and out in their respective slots in the cylinder, and to allow air to act as a bearing between the tips of the vanes and the inner wall of the cylinder, especially where the distance between the rotor and the eccentric cylinder is at a minimum. This is illustrated below. The vanes should, however be rigid enough not to flex so much that air leaks past them. They should have low friction, and, ideally, even be self-lubricating or require no lubrication, yet be able to absorb without significant deformation the inevitable heat they will be subjected to. One suitable vane material has been found to be vinyl ester, sold under the trade name Orkot HT. Molybdinumisulfite vanes have also tested well, and have the advantage of being self-lubricating. Another material that has tested well is graphite-filled Micarta, Grade 400, with a phenolic cotton base. Normal design methods may, however, be used to choose other material for the vanes.

Figure 2:
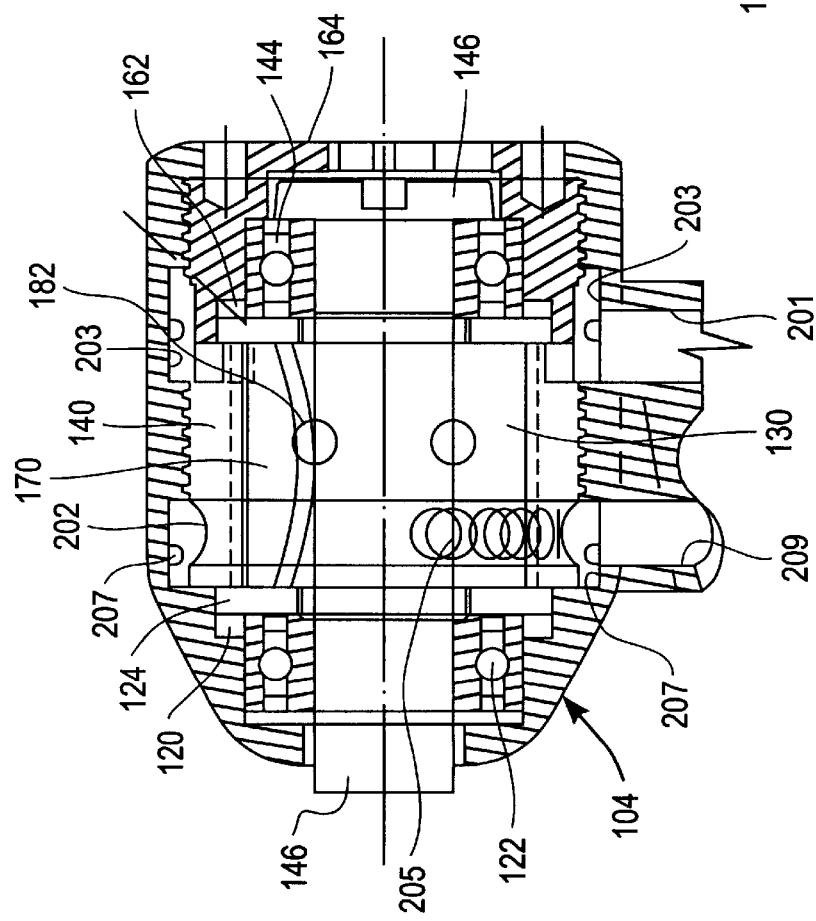
FIG. 2 is an enlarged, cross-sectional side view of a head of the handpiece containing the assembled vane motor according to the invention.

FIG. 2 is a cross-sectional side view of the head 104 with the assembled motor mounted within it. The various motor parts and their relationship to one another have already been explained in reference to FIG. 1. What can be seen more clearly in FIG. 2, however, is the inflow and outflow air paths used in the invention.

Pressurized air flows into the motor via an inlet channel or conduit 201, typically formed in the handle of the handpiece. This channel 201 opens into an annular recess 203 that extends around the outer edge of the cylinder 140. Intake air then passes through inlet ports (one or more) in the cylinder. Air exits the motor via outlet ports 205 formed as holes in the cylinder. These outlet ports open into an annular outlet channel, which is formed by an annular outlet recess 207 that is machined into the head, and an adjacent annular groove 202 in the cylinder 140 near its inner edge. Air then exits the motor to the surrounding environment via an exhaust channel or conduit 209, as in conventional devices.

In order to achieve the best motor efficiency and highest torque, it is important for enough intake air to be able to reach the motor, and fast enough, and for air to be exhausted rapidly, without significant reduction of pressure differential between the inlet and exhaust. In this respect, the annular groove 202 and recess 207 together form a large and efficient outlet chamber for exhaust air. It would be possible, however, for either the groove or recess to be omitted if the other annular opening is large enough. Similarly, the single annular intake channel 203 will in most cases allow inflow of more than enough air to drive the motor over its full range of operating speeds. If more air is needed, however, then it would also be possible to include an annular intake groove near the outer edge of the cylinder, similar to the groove 202, in order to increase the volume of the intake chamber. The various ports are illustrated and described in greater detail below.

One additional but important advantage of the arrangement of intake and outlet air channels in the preferred embodiment of the invention is that there is no need to rotationally align the intake and outlet ports with any part if the head in order to ensure proper air flow. This eliminates the need for keys and other means of arranging for precise angular mounting of the cylinder within the head in order to achieve proper port alignment.

Figure 3:
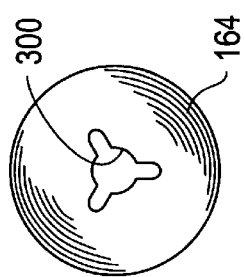
FIG. 3 shows a motor end cap used in the invention.

FIG. 3 illustrates one embodiment of the end cap 164, viewed from the outside of the assembled motor and head. As in standard devices, a hole 300 is included through the end cap to allow tightening of the tool 166 when it is inserted into the handpiece, as well as tightening of the end cap itself, which is preferably screwed into the head.

The invention allows for three or more vanes 170a, 170b to be included in the motor. Two different choices are illustrated here: the three-vane and six-vane embodiments. Four, five, and even more than six vanes may even be included; for any given application, the best number can be chosen using normal experimentation. The inventors have determined through testing, however, that the three- and six-vane embodiments will in most cases have particular advantages: The three-vane embodiment has proven to provide the greatest torque, especially at low cutting speeds, whereas the six-vane embodiment, although producing slightly less torque, was better at self-starting and ran more smoothly (less variation in rotational speed).

Figure 4:
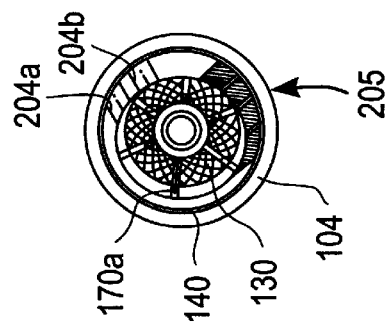
FIGS. 4 and 5 are partially cross-sectional end views of a rotor, eccentric cylinder, vanes, and head for a six- and three-vane embodiment of the invention, respectively.
Figure 5:
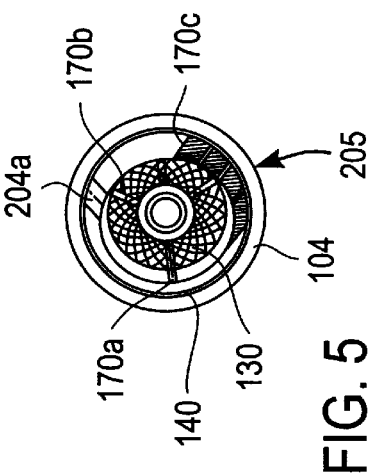

FIG. 4 is an end view of the rotor 130, cylinder 140, vanes 170a, and head 104 for the six-vane embodiment of the invention. FIG. 5 shows the same view of the three-vane embodiment. In both cases, at least one inlet port 204a, 204b is opens through the cylinder and directs pressurized air towards the vanes. Tests have indicated that multiple inlet ports provide better torque than one, although the motor will work with only one inlet port. Multiple input ports allow faster air intake, which increases both torque production and self-starting effectiveness. FIG. 5 shows a single inlet port for the sake of clarity only. Furthermore, the same effect may be achieved by forming the inlet port as a single, wider inlet slit rather than separate, multiple inlet holes.

Of course, air entering the motor chamber (the space between the outer surface of the rotor and the inner surface of the eccentric cylinder, must also be efficiently evacuated from the chamber in order to avoid a loss of the pressure differential that primarily drives the rotor. As is described above, outlet ports labeled collectively as 205, are therefore formed as holes through the cylinder wall. In FIGS. 4 and 5, four separate outlet channels are shown. This is of course not necessary; rather, a single, outlet slit could be cut into the cylinder, or a different number of separate channels could be formed. The only requirement is that the exhaust (outlet channels) should provide as little resistance as possible to the flow of air out of the cylinder and head once the vane it has driven has reached the end of its duty stroke (described in greater detail below).

FIG. 6 is a perspective view of the rotor 130 and of one of the vanes 170a. This figure shows more clearly the longitudinal grooves 602, 604 formed on the inner surface of the rotor to receive the balls 180, 182 (FIGS. 1 and 2) and allow the rotor to float longitudinally on its shaft. As FIG. 6 illustrates, the vanes are preferably substantially rectangular, but with a curved, convex lower surface. The lower curve of each vane allows less of the rotor to have to be cut away at the edges and thus ensures both that there is always enough of the vane in its respective slot to avoid wobbling. The curvature also ensures that the slots do not have to be cut so deeply across the entire width of the rotor 130 that it would loose strength and rigidity. Note that the vanes must extend all the vane to both ends of the rotor in order to prevent air leakage around their edges.

FIG. 7 is a simplified cross-sectional end view of the rotor 130 within the eccentric cylinder 140. FIG. 7 illustrates some of the unique vane and porting geometry used in the invention to achieve some of its advantages, such as greater torque even at low speed. Merely for the sake of simplicity and ease of illustration, only one inlet port 204 and one outlet port 205 are shown. The analysis and description below will apply, however, to any number of ports. To the extent that any modification would even be necessary, then these will be obvious to those skilled in the art of manufacturing dental and medical handpieces. The three-vane embodiment is illustrated simply for the sake of clarity—showing six vanes would almost double the complication of the figure without adding anything to the analysis. The six-vane (indeed, any other number of vanes greater than three) embodiment of the invention will operate in the same manner and can be analyzed in the same way as for the illustrated three-vane embodiment.

The radial gap between the rotor 130 and the shaft 146, indicated by reference number 700, has the average distance ε, which, in one prototype of the invention, was only 0.025–0.051 mm (0.001–0.002 inches), as is mentioned above.

In the preferred embodiment of the invention, small channels or grooves 702a, 702b, 702c are made (for example, simply by drilling) to connect the bottom of the vane slots 172a, 172b, 172c with the gap 700. These channels thus provide an opening between the slots and to either the outside environment, or at least to a secondary volume of air located radially within the rotor. To see the advantage of this, consider the vane 172c, which is substantially fully depressed in its slot 172c and thus fills the entire—or in any event almost all of—the slot cavity. Assume further that there were no channel 702c, which is the case in existing vane motors. As the rotor rotates counter-clockwise (viewed as in FIG. 7, and indicated by the arrow 704), to the region where the clearance to the inner wall of the cylinder is greater (for example, where vane 170a is shown), the only force that would act to urge the vane 170c out of the slot would be the centrifugal force caused by the rotation itself. On the other hand, unless the tolerance of the vane in the slot is very loose, a partial vacuum will also form beneath the vane and will hinder or at least slow the vane's extension. The faster the rotor rotates, the stronger the vacuum will be.

Conventional vane motors attempt to overcome this by including springs that are compressed beneath each vane. This of course adds to the weight, inertia and complexity of such rotors. It also means that a force in addition to the normal centrifugal force is always forcing the outer edge of every vane against the inner surface of the cylinder. This of course increases the wear on the vanes. Some motors then require additional bearing cylinders to reduce this wear, which makes things even worse, and so on.

The channels 702a, 702b, 702c, beneath each vane according to the invention enable the invention to avoid or at least greatly reduce any vacuum effect, with no need for additional biasing members such as springs. This also allows for smaller tolerances between the vanes and the slots, with no significant loss of retraction and extension speed.

Yet another advantage of the channels 702a, 702b, 702c is that, as a vane is pushed inward, the air beneath it is forced out through the respective channel, into the opening 700, and will increase the air pressure in this annular opening, especially if the opening is completely sealed off from the ambient air. The inward movement of one vane will thus help extend the other vanes and hold them in the correct starting position. The "pumping" effect also increases the speed at which other vanes can extend.

In the three-vane embodiment of the invention, the closest point, measured angularly in the direction of rotation, of any outlet port 205, to the nearest point of any inlet port 204, is at least 120°. For motors with more vanes than three, this separation between the inlet and outlet should be at least equal to the angular separation between the vanes.

An X-Y-Z coordinate system is shown in FIG. 7. The X-axis is the axis of rotation X1 of the rotor. The central axis X2 of the interior bore of the eccentric cylinder 140 is offset from but parallel to X1. The Y axis extends from the X axis through the point of minimum gap between the rotor and the inner surface of the eccentric cylinder 140.

One advantage of the invention is that the inlet port(s) 204, and preferably even the outlet ports 205, can be drilled through the wall of the cylinder 140 along a line in the Y-Z plane, that is, perpendicular to the X axis. This means that inlet air can be directed directly against the vanes and outer surface of the rotor, and can thus directly impart momentum in the tangential direction of rotation to both. This helps the rotor according to the invention to self-start.

In FIG. 7, angular position measured from the positive Y-axis is indicated as the angle α. In order to maximize the torque and self-starting ability of the rotor, it has been calculated that the inlet port(s) 204 for the three-vane motor should be made so that if only one port is used it should be in the range α=70–80°. Normal theoretical and experimental methods may be used to determine the best placement for ports for rotors with more vanes than three.

In the three-vane embodiment, three pressure chambers are formed between the rotor and the cylinder. These chambers are the spaces whose three end "walls" are the three vanes themselves. Because of the efficient design of the motor according to the invention, the tolerances within the motor chamber can be kept much smaller than in prior art designs. In one prototype of the invention, for example, the narrowest distance between the rotor and the inner surface of the cylinder (at position α=0 in FIG. 7), was as small as 0.0254 mm (0.001 in.). This is so small that this region essentially forms a stop or wall, since only a negligible amount of air can pass this gap. The maximum spacing between the rotor and the stator (at position α=180 degrees in FIG. 7) was only 0.8636 mm (0.0341 in.).

As soon as the first vane 170a (as shown in FIG. 7) passes the input port 204, the pressure of the first chamber (the space between the vane and the gap at α=0) will increase to the input pressure $P_{IN}$ and the force pushing in the direction of rotation, by this chamber, will be determined by the formula:

$$F=P_{IN}*\delta 1*L$$

where:
L is the length of the vane;
δ1 is the distance the vane 170a is extended, that is, the height of the chamber.

When vane 170c passes the angular zero position, there will be increasing force opposing the rotation the more it extends as the motor rotates. The force on vane 170c will, however, remain less than the force on vane 170a until the vane 170a reaches the position α=240°. Additional outlets can be placed beyond that angle, but preferably no closer than σ degrees from the first inlet port location. Until then the force contributed by the pressure chamber between the vanes 170a, 170c will be:

$$F=P_{IN}*(\delta 1-\delta 2)*L$$

where δ2 is the extension of the vane 170c.

The first-encountered one of the outlet port(s) 205 should therefore preferably begin at this angular position of α=240°, or later.

Once vane 170a crosses the output port 205 position, pressure in this chamber will decrease to ambient pressure $P_{OUT}$ and there be will no longer be any net force contributed by the pressure chamber between the vanes 170a, 170c. Thanks to the port arrangement according to the invention, the duty stroke of each vane has proven in tests to be as high as 240°, that is, twice the angular separation of the vanes, and sometimes even higher.

Three factors reduce leakage of air between chambers, that is, past the vanes. The first is the sealing effect of the vanes themselves. The second is a function of the tolerances between the rotor and the cylinder—the smaller the clearance is between the two respective surfaces at the narrowest point, the better the motor's performance will be. The third is that the gap between the rotor and the end caps—although enough to allow sufficient "floating" (see above)—is very small, on the order of less than 0.0254 mm (0.0001 in.).

Figure 8A:
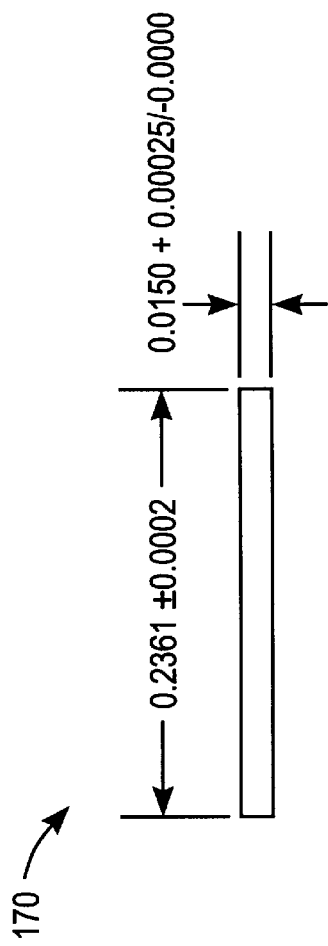
FIGS. 8A and 8B show, respectively, an end view and a side view a vane.
Figure 8B:
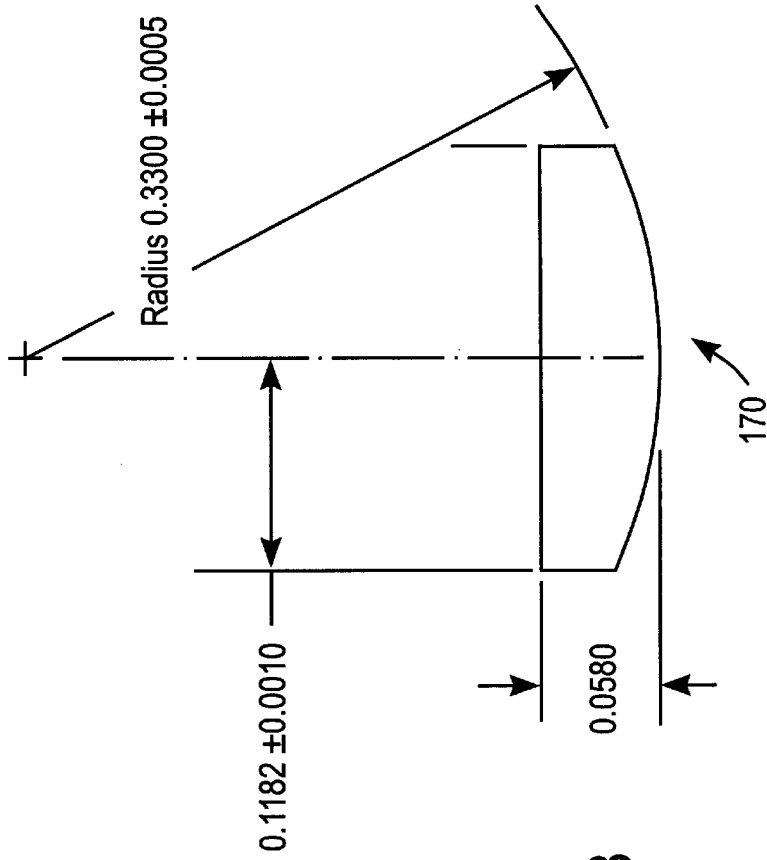

In order to illustrate the compactness of the vane motor according to the invention, FIGS. 8A, 8B and 9–12 show actual dimensions used in one working prototype of the invention. FIG. 8A is an end view of one vane 170; FIG. 8B is a side view of the same vane.

Figure 9:
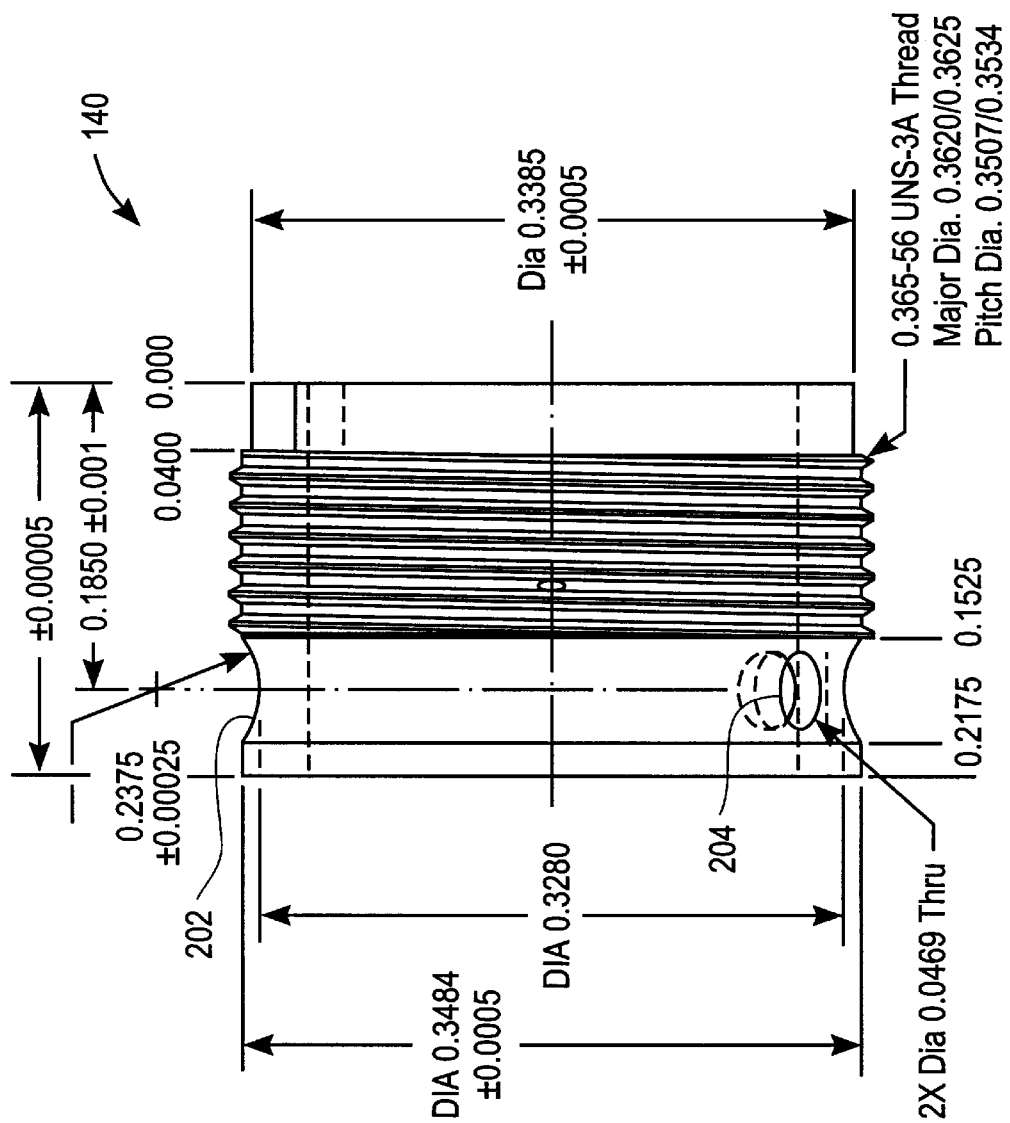
FIG. 9 is a side view of the eccentric cylinder, including the dimensions of the cylinder used in a working prototype of the invention.

FIG. 9 shows the dimensions of an eccentric cylinder 140 used for both the three-vane and six-vane embodiments of the invention. Note that the outer diameter of the cylinder was no more than 8.89 mm (0.35 inch).

Figure 10:
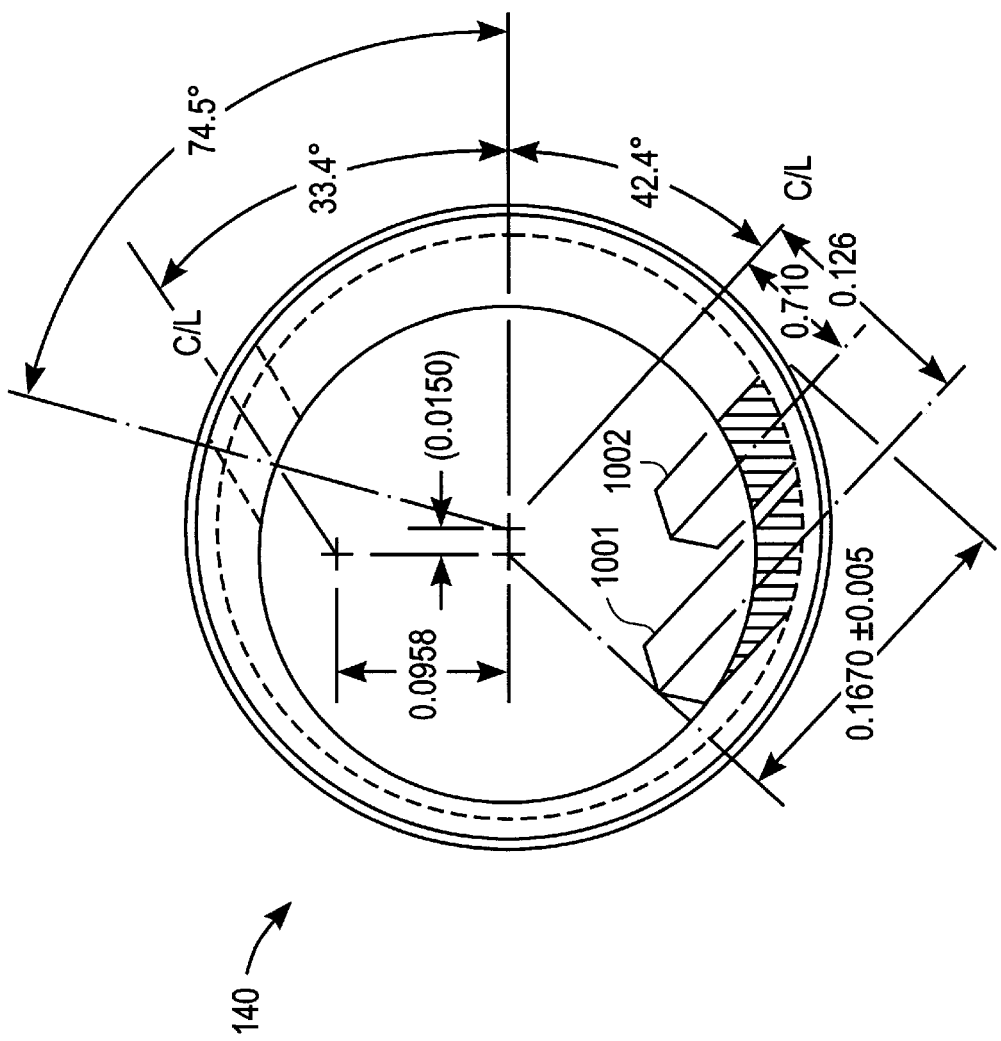
FIGS. 10 and 11 show the placement of the inlet and outlet ports for a three- and six-vane configuration, respectively.
Figure 11:
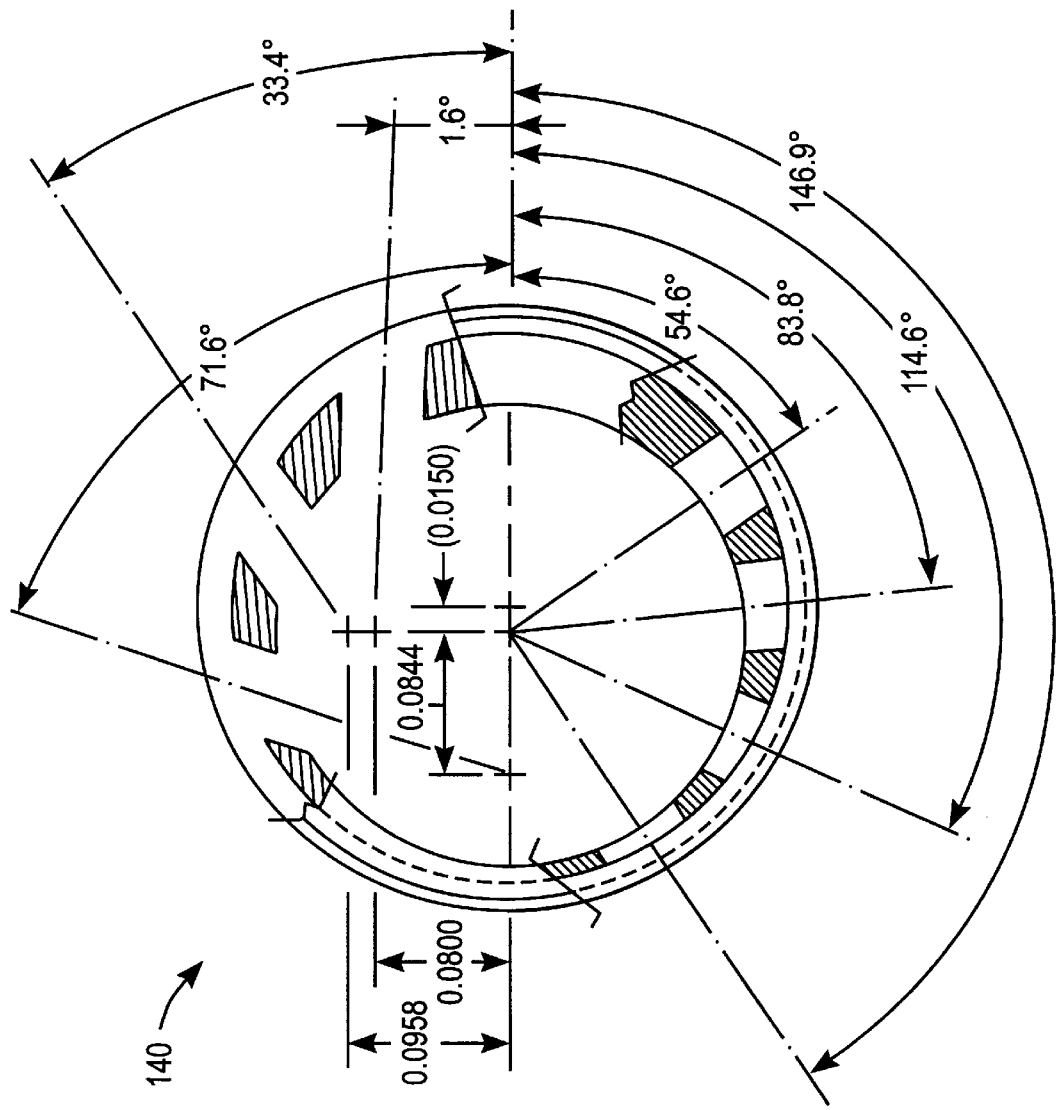

FIGS. 10 and 11 show the placement of the inlet and outlet ports for a three- and six-vane configuration, respectively. To make these ports in the cylinder 140, holes were drilled through its wall. Shadow drill bits 1001 and 1002 are indicated to illustrate the alignment of the center lines (C/L) of the various ports, as well as the "target" points for drilling the other port holes with the same drill bits. The offset that determined the eccentricity of the inner surface of the cylinder—the distance between X1 and X2, was only 0.381 mm (0.015 inch).

Figure 12:
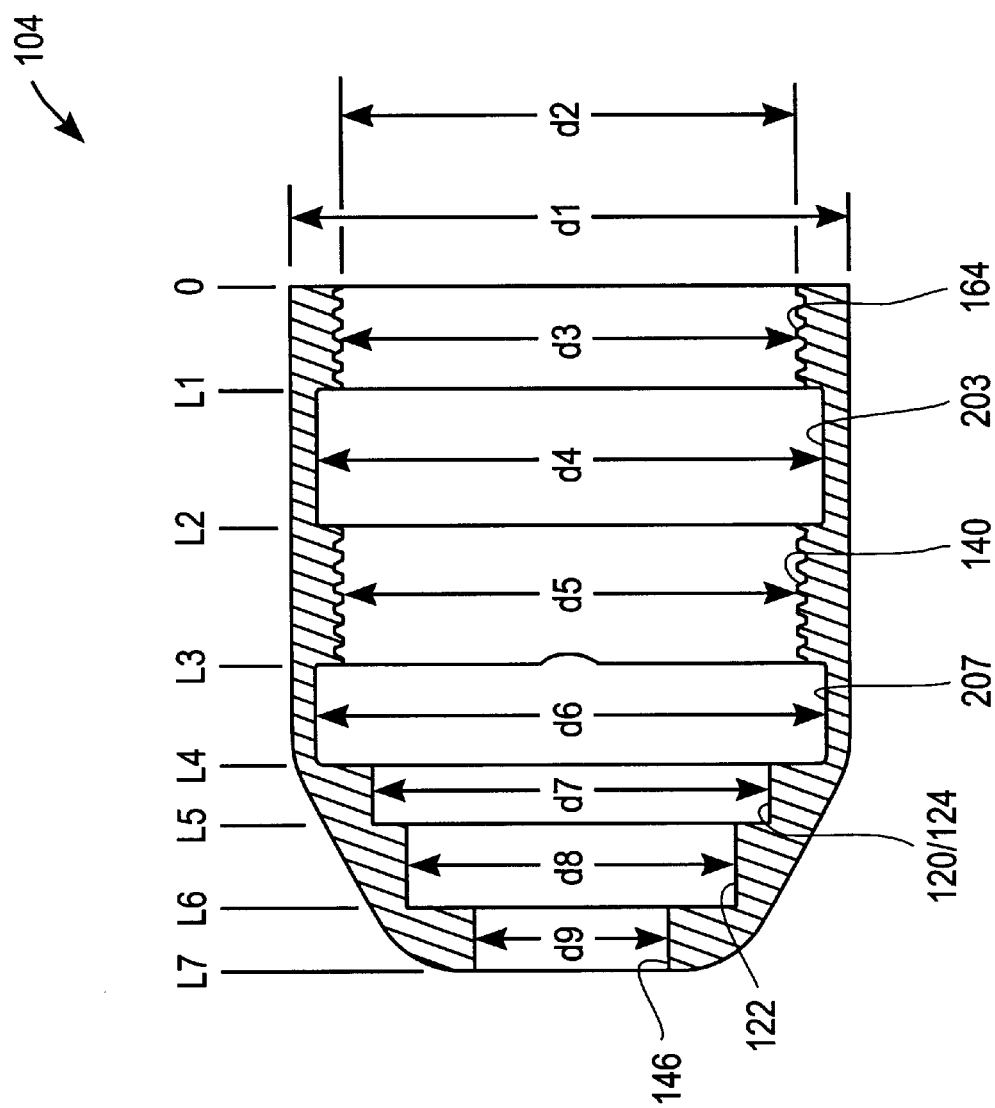
FIG. 12 is a cross-sectional side view of a handpiece head into which the motor according to the invention can be fitted.

FIG. 12 is a cross-sectional side view of the head with the motor and all its related parts removed. A vertical datum line is indicated as distance 0; linear distances the datum are indicated as lengths L1–L7. Diameters of the various cylindrical interior portions of the head are indicated as d1–d9, including the total external diameter d8 of the entire head. In one prototype of the invention, the distance, measured from the datum, were as follows:

| Distance | Value |
| --- | --- |
| L1 | 2.238 mm (0.0881 in.) |
| L2 | 5.080 mm (0.2000 in.) |
| L3 | 7.938 mm (0.3125 in.) |
| L4 | 10.100 mm (0.3975 in.) |
| L5 | 11.240 mm (0.4425 in.) |
| L6 | 13.157 mm (0.5180 in.) |
| L7 | 14.478 mm (0.5700 in) |

The various diameters, were as follows:

| Diameter | Value | |
| --- | --- | --- |
| d1 | 10.820 mm (0.4260 in.) | |
| d2 = d3* = d5* | 9.271 mm (0.3650 in.) | (*major diameters) |
| d4 = d6 | 9.868 mm (0.3885 in.) | |
| d7 | 7.950 mm (0.3130 in) | |
| d8 | 6.350 mm (0.2500 in.) | |
| d9 | 3.721 mm (0.1465 in) | |

In FIG. 12, the various cavities are labeled with the reference number of the element they are to receive. For example, the bearing 122 will fit in the cavities with the diameter d8. Of course, these dimensions are not necessary to the invention; the various cylindrical recesses d2–d9 will, for example, depend on which threading one chooses for the cylinder 140 and end cap 164, how large a shaft 164 one chooses, and so on. What is important to notice, however, is that the motor according to the invention can be housed completely within a dental and medical handpiece head of normal size.

FIGS. 14–18 show the results of various tests comparing the motor according to the invention and a widely used conventional, commercially available dental handpiece incorporating a well-known, standard turbine motor. In the captions, "INV" represents data for the invention and "CONV" represents data for the known handpiece.

Figure 13:
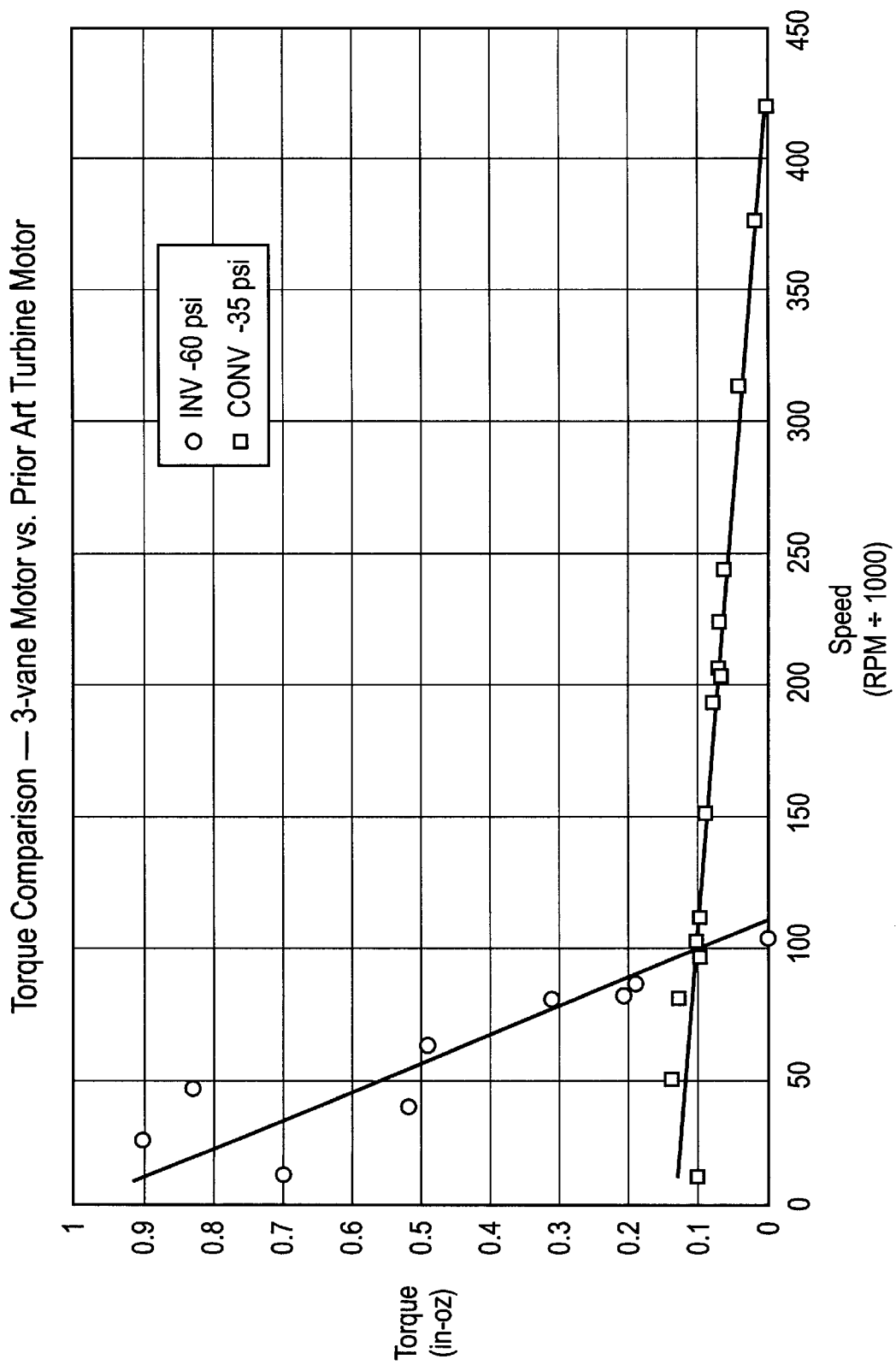
FIGS. 13–18 show the results of various tests comparing the motor according to the invention with a widely used conventional dental handpiece that incorporates a known vane motor.
Figure 14:
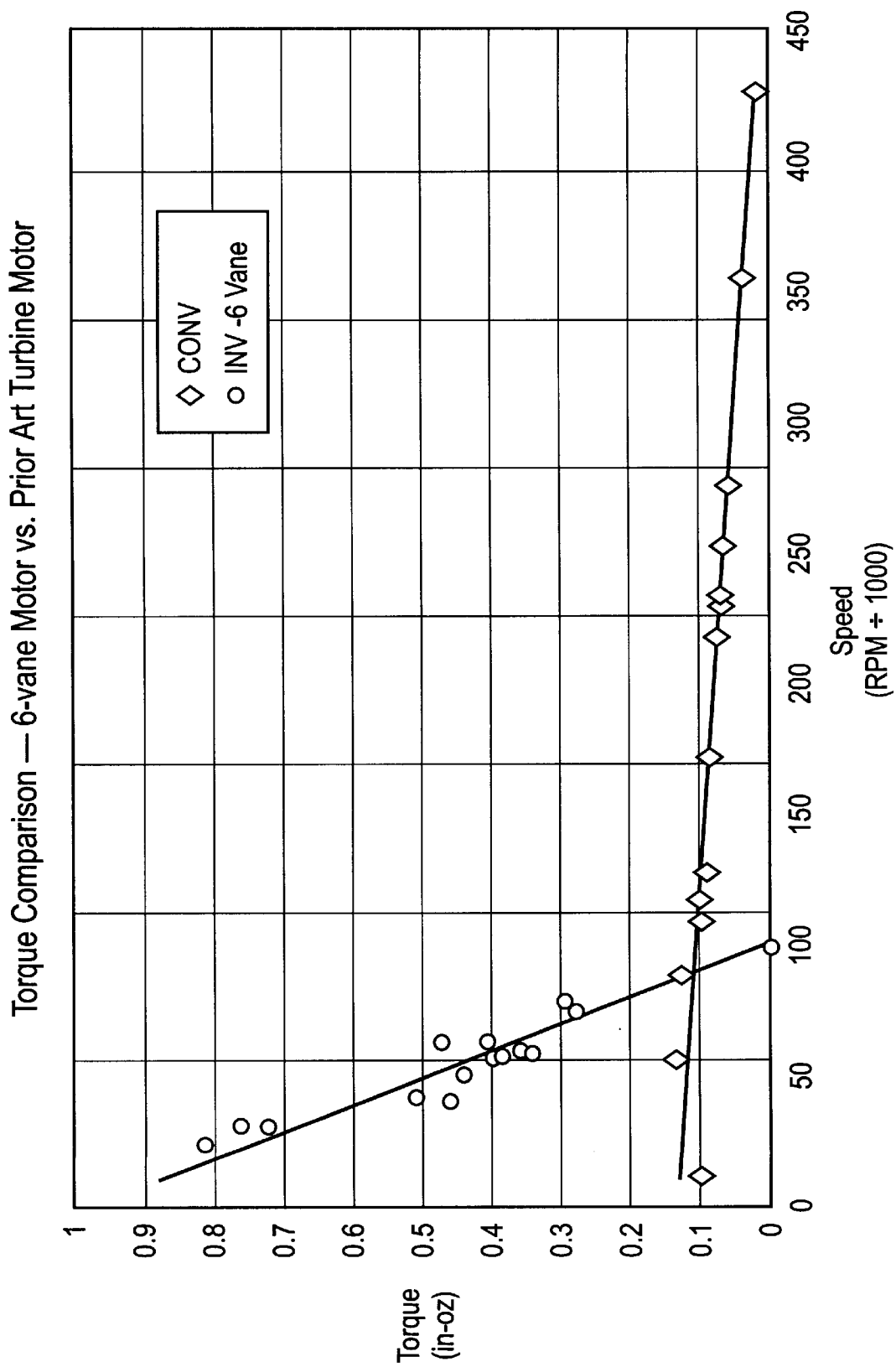

FIGS. 13 and 14 show a test comparison of torque between the conventional handpiece motor, on the one hand, and the three- and six-vane motors, respectively, according to the invention as a function of rotational speed in thousands of rpm's The conventional handpiece was operated at a supplied air pressure of 35 p.s.i., according to the manufacturer's operating specifications. In both cases, the invention was operated at 60 p.s.i. This in itself brings out another advantage of the invention, namely, that it may be operated normally at a much higher input pressure than conventional handpieces. This in turn increases efficiency. Comparative tests of the invention at 35 p.s.i. showed, moreover, similar qualitative improvements over the conventional handpiece. The result of one practical comparative test are described below in connection with the explanation of FIG. 17.

As FIGS. 13 and 14 show, the vane motor according to the invention has much greater torque capabilities at the lower speed that it preferably operates in. This low-rpm/high-torque capability is particularly useful for cutting procedures such as tooth and bone reductions: It allows for efficient cutting while avoiding much of the heat in both the device and the surrounding tissue, as well as the friction abrasion, caused by conventional high-speed operation. As the figures show, the maximum unloaded speed of the three-vane motor was about 103,000 rpm, which is much lower than the 430,000 rpm unloaded speed of the conventional device. The maximum speed of the 6-vane motor was about 89,000 rpm.

Figure 15:
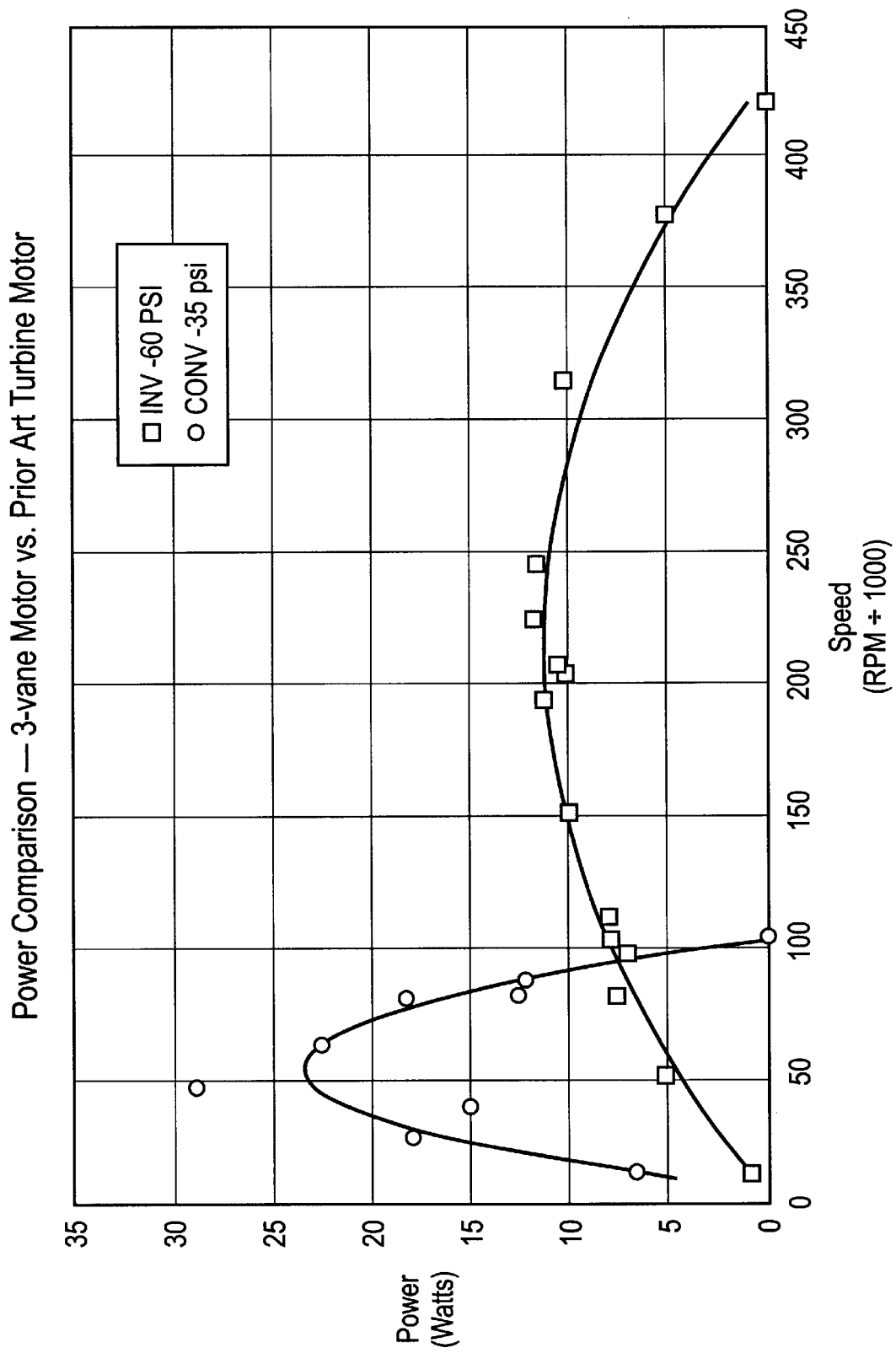
Figure 16:
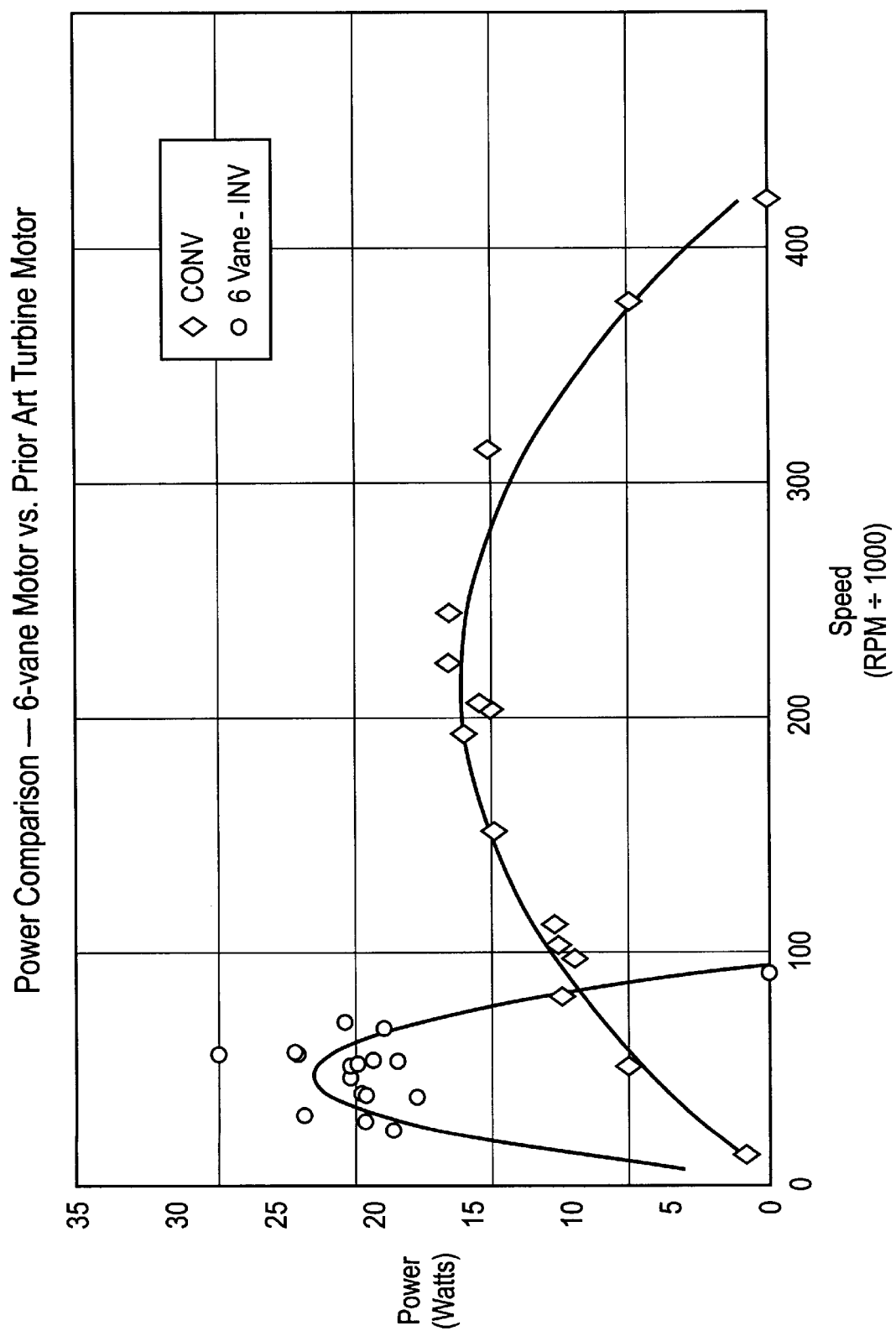

FIGS. 15 and 16 compare the power generated by the same vane motors according to the invention and the same conventional motor. Again, one can note that the vane motors according to the invention not only achieved higher power, but could do so at lower speeds.

Figure 17:
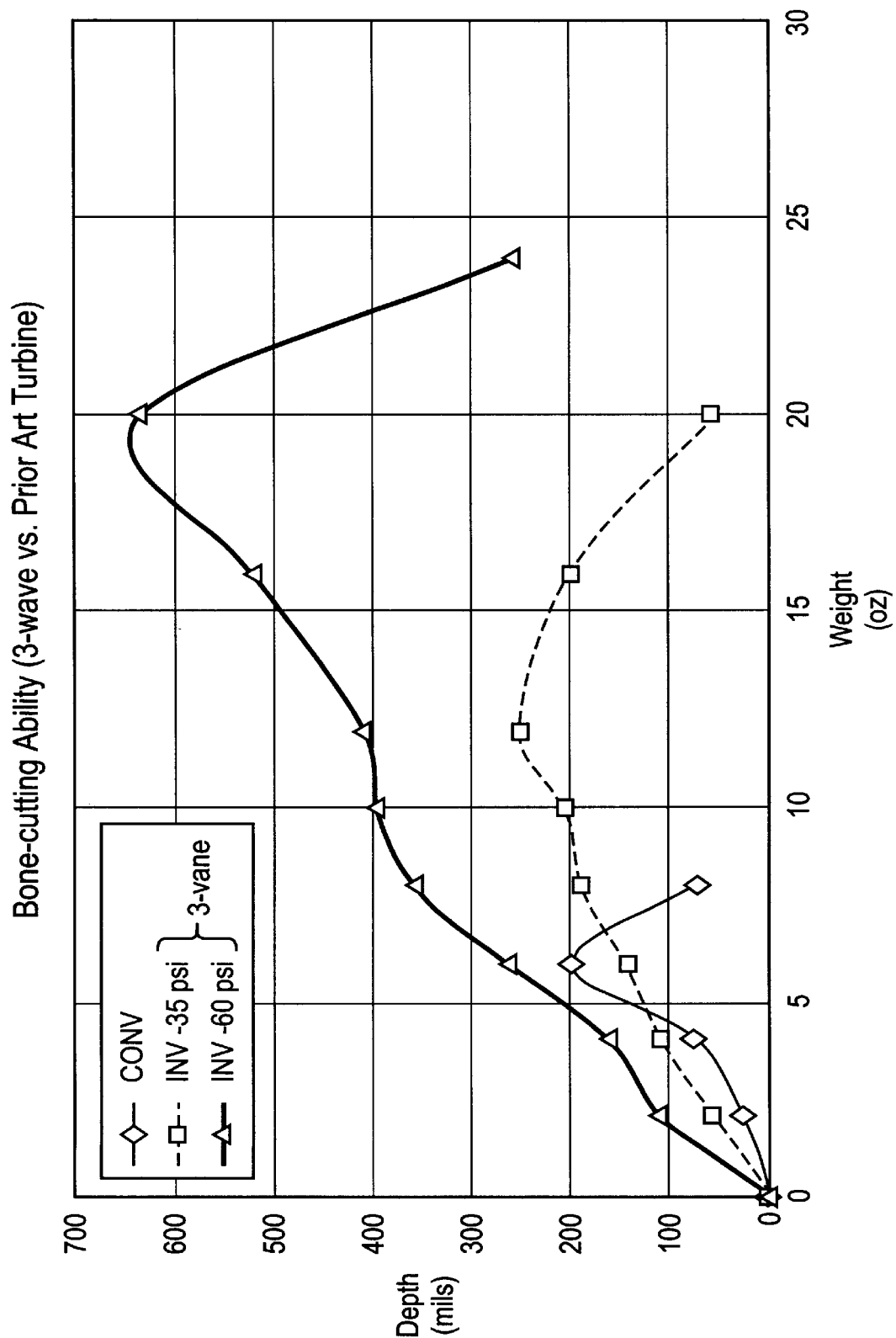
Figure 18:
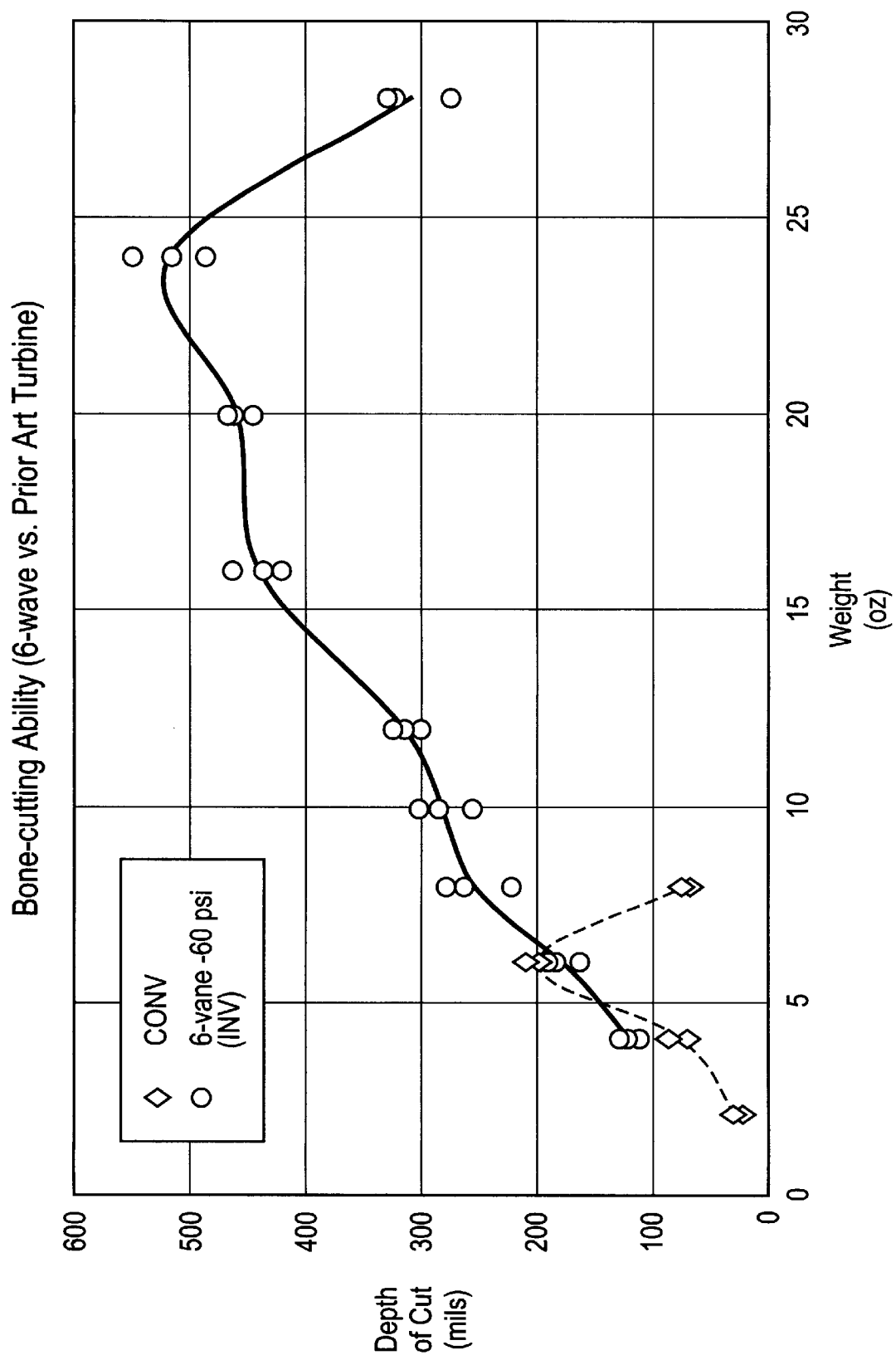

As a practical test of the handpiece according to the invention with the conventional device, their respective abilities to cut into bone were measured. FIGS. 17 and 18 show, respectively, the results for the three-vane and six-vane motors according to the invention. The test was carried out as follows:

A special test stand was constructed that could hold a handpiece, with motor, in position, with a burr located so that it could be lowered onto a surface. Various loads (the "weight"), which were varied in two-ounce increments, were then applied to the handpiece. With the load in place, the motor was started, and the handpiece gently lowered and let go onto the surface of a bone, with the applied weight forcing the weight onto the bone. The burr that was used in all of these tests was one chosen as a standard and provided by the manufacturer of the conventional device. The burr was positioned such that it extended 2.54 mm (0.1 inches) in from the edge of the bone surface. The burr was then allowed to cut into the material for a period of 5 seconds. Three measurements were made for each load. The depth of cut made by the burr was then carefully measured after the runs were completed; the average values are plotted in FIGS. 17 and 18.

As FIG. 17 shows, the three-vane embodiment of the invention, even at the same 35 p.s.i. supply pressure, achieved deeper cuts, and continued to do so even when loaded far beyond the point at which the conventional device stalled and could no longer operate at all. At the 60 p.s.i.

supply pressure that the invention can and preferably does operate at, the cutting ability of the invention was dramatically better and over a much greater load range than was possible using the conventional device.

Measurements of cutting ability for the six-vane embodiment of the invention are plotted in FIG. 18, along with the measurements made for the same conventional handpiece. As was the case with the three-vane embodiment of the invention, the six-vane embodiment removed bone material much more effectively, and over a much larger load range, than the conventional device.

A comparison of the three- and six-vane embodiments of the invention (FIGS. 17 and 18) reveals that the three-vane embodiment had the best cutting depth at all low loads, up to about 20 oz. The six-vane embodiment, however, was able to sustain higher loads before stalling.

FIGS. 13–16 illustrate certain other advantages of the invention. For example, notice that both the three-vane and six-vane embodiments of the invention are able to operate, that is, drive the tool sufficiently to cut bone, over a wide range of speeds, exceeding the conventional turbine motor in both power and torque at all speeds up to at least 80,000 rpm's, and in some cases up to 100,000 rpm's. This means in turn that the speed of the motor according to the invention can be varied, using the controller 110 (FIG. 1) to vary air delivery. This is in contrast to conventional turbine-driven devices, which must usually be operated at a fixed pressure, resulting in a fixed maximum speed. This is also in contrast to conventional handle-mounted vane motors, which, in addition to their other disadvantages, typically have a maximum operating speed of only around 20,000 rpm's.

One of the other major advantages of the invention is its compactness. As several of the figures show, the vane motor according to the invention can be mounted completely within a headpiece head of standard size. It is able to drive the tool 166 directly, that is, with a single shaft for both the rotor and tool. It would, however, be possible to mount the vane motor according to the invention within the handle, providing it with some known arrangement for transmitting torque to the tool. Even in such cases, the other advantages of the invention, such as efficient air porting, high torque at low speeds, floating of the rotor on the shaft, avoidance of a vacuum forming under the vanes, etc., can still lead to a device that is easier to work with and more efficient than existing designs.

We claim:

1. An arrangement for driving a rotary dental or medical tool comprising:

a source of pressurized gas;

a handpiece that includes a handle and a head, which is attached to the handle;

a rotary vane motor, to which the tool is attached and which is mounted within the head of the handpiece; and an inlet conduit leading the pressurized gas to the vane motor;

a cylindrical rotor;

a cylindrical stator with an eccentric, cylindrical, longitudinally extending bore, in which the rotor is mounted, the rotor and stator being concentric about a longitudinal axis, which is the axis of rotation of the rotor;

a plurality of unbiased vanes mounted in corresponding, substantially lengthwise-extending slots formed in the rotor, the unbiased vanes being substantially freely movable in their respective slots in a radial direction that is perpendicular to the axis of rotation;

an inlet port and an outlet port formed as openings through the stator in which:

an annular space between an outer surface of the rotor and an inner surface of the bore of the stator is uninterrupted, an air bearing thereby being formed between a radially outermost tip surface of each vane and an inner surface of the bore of the stator when the rotor rotates within the stator.

2. An arrangement as in claim 1, in which the inlet port is formed as a bore that extends mainly in a plane that is perpendicular to the axis of rotation of the rotor, whereby inlet gas entering through the inlet port is directed substantially directly against the vanes and outer surface of the rotor, thereby directly imparting momentum in a tangential direction of rotation.

3. An arrangement as in claim 2, in which:

the vanes have a uniform relative angular separation of σ=360/n degrees, where n is the number of vanes;

the inlet port is located within σ degrees from an angular zero position, the angular zero position being defined by a line that extends perpendicularly from the axis of rotation through a closest point between the outer surface of the rotor and the inner surface of the eccentric cylinder; and the outlet port is located at least σ degrees away from the inlet port and σ/2 beyond an angular position 180° away from the angular zero position, measured in the direction of rotation of the rotor.

4. An arrangement as in claim 3, in which:

the inlet port located within σ degrees from the angular zero position is a first of a plurality of inlet ports, the remaining inlet ports being provided at locations both before and after the angular location of the first inlet port, beyond the angular zero position and before σ/2 degrees before the 180° angular position; and the outlet port located at least σ degrees away from the inlet port is a first outlet port of a plurality of outlet ports and σ/2 beyond an angular position 180° away from the angular zero position, the remaining outlet ports being provided at locations beyond the angular location of the first outlet port and before σ degrees before the first inlet port.

5. An arrangement as in claim 1, further including:

an annular inlet channel located between the stator and the head and connecting the inlet port via the inlet conduit with the source of pressurized gas; and and an annular outlet channel located between the stator and the head and connecting the outlet port via an outlet conduit with the ambient environment;

whereby communication of pressurized gas with the inlet port and of exhaust gas from the vane motor with the ambient environment is independent of the angular alignment of the vane motor within the head of the handpiece.

6. An arrangement as in claim 1, further comprising:

a shaft, on which the rotor is mounted;

key means for rotationally securing the rotor to the shaft and for allowing movement of the rotor in the longitudinal direction on the shaft;

end caps restraining movement of the rotor on the shaft;

a longitudinal gap between the rotor and the end caps, the rotor thereby assuming a balanced position when rotating.

7. An arrangement as in claim 1, further including:

a shaft, on which the rotor is mounted and to which the tool is securely attachable, the axis of rotation of the rotor thereby also forming an axis of rotation of the tool mounted and the vane motor thereby directly driving the tool.

8. An arrangement as in claim 1, further including a control means for user-controlled variation of the amount of pressurized gas delivered to the vane motor and thereby for user control of the rotational speed of the vane motor and the tool.

9. An arrangement for driving a rotary dental or medical tool comprising:

a source of pressurized gas;

a handpiece that includes a handle and a head, which is attached to the handle;

a rotary vane motor, to which the tool is attached;

a conduit leading the pressurized gas to the vane motor;

a cylindrical rotor;

a cylindrical stator with an eccentric, cylindrical, longitudinally extending bore, in which the rotor is mounted, the rotor and stator being concentric about a longitudinal axis, which is the axis of rotation of the rotor;

a plurality of vanes mounted in corresponding, substantially lengthwise-extending slots formed in the rotor, the vanes being movable in their respective slots in a radial direction that is perpendicular to the axis of rotation;

at least one inlet port and at least one outlet port formed as openings through the stator;

a shaft, on which the rotor is mounted and to which the tool is securely attachable, the axis of rotation of the rotor thereby also forming an axis of rotation of the tool mounted and the vane motor thereby directly driving the tool a radial gap between the rotor and the shaft;

key means for rotationally securing the rotor to the shaft;

a channel connecting an inner portion of each slot with the radial gap, the channels and the gap thereby together forming means for reducing any vacuum formed under each vane as it extends in its slot;

key means for rotationally securing the rotor to the shaft and for allowing movement of the rotor in the longitudinal direction on the shaft;

end caps restraining movement of the rotor on the shaft floating;

a longitudinal gap between the rotor and the end caps, the rotor thereby assuming a balanced position when rotating;

in which:

the vane motor is mounted within the head of the handpiece;

each inlet port is formed as a bore that extends mainly in a plane that is perpendicular to the axis of rotation of the rotor, whereby inlet gas entering through each inlet port is directed substantially directly against the vanes and outer surface of the rotor, thereby directly imparting momentum in a tangential direction of rotation;

the vanes have a uniform relative angular separation of σ=360/n degrees, where n is the number of vanes;

a first one of the inlet ports is located less than σ degrees of an angular zero position, the angular zero position being defined by a line that extends perpendicularly from the axis of rotation through a closest point between the outer surface of the rotor and the inner surface of the eccentric cylinder; and a first one of the outlet ports is located at least σ degrees away from the inlet port and σ/2 beyond an angular position 180° away from the angular zero position, measured in the direction of rotation of the rotor.

10. An arrangement for driving a rotary dental or medical tool comprising:

a source of pressurized gas;

a handpiece that includes a handle and a head, which is attached to the handle;

a rotary vane motor, to which the tool is attached and which is mounted within the head of the handpiece;

an inlet conduit leading the pressurized gas to the vane motor;

a cylindrical rotor;

a cylindrical stator with an eccentric, cylindrical, longitudinally extending bore, in which the rotor is mounted, the rotor and stator being concentric about a longitudinal axis, which is the axis of rotation of the rotor;

a plurality of vanes mounted in corresponding, substantially lengthwise-extending slots formed in the rotor, the vanes being movable in their respective slots in a radial direction that is perpendicular to the axis of rotation; and an inlet port and an outlet port formed as openings through the stator;

a shaft, on which the rotor is mounted;

a radial gap between the rotor and the shaft;

key means for rotationally securing the rotor to the shaft; and a channel connecting an inner portion of each slot with the radial gap, the channels and the gap thereby together forming means for reducing any vacuum formed under each vane as it extends in its slot.

11. An arrangement for driving a rotary dental or medical tool comprising:

a source of pressurized gas;

a handpiece that includes a handle and a head, which is attached to the handle;

a rotary vane motor, to which the tool is attached and which is mounted within the head of the handpiece; and an inlet conduit leading the pressurized gas to the vane motor;

a cylindrical rotor;

a cylindrical stator with an eccentric, cylindrical, longitudinally extending bore, in which the rotor is mounted, the rotor and stator being concentric about a longitudinal axis, which is the axis of rotation of the rotor;

a plurality of vanes mounted in corresponding, substantially lengthwise-extending slots formed in the rotor, the vanes being substantially freely movable in their respective slots in a radial direction that is perpendicular to the axis of rotation;

an inlet port and an outlet port formed as openings through the stator in which:

an annular space between an outer surface of the rotor and an inner surface of the bore of the stator is uninterrupted, an air bearing thereby being formed between a radially outermost tip surface of each vane and an inner surface of the bore of the stator when the rotor rotates within the stator.

12. An arrangement for driving a rotary dental or medical tool comprising:

a source of pressurized gas;

a handpiece that includes a handle and a head, which is attached to the handle;

a rotary vane motor, to which the tool is attached and which is mounted within the head of the handpiece; and an inlet conduit leading the pressurized gas to the vane motor;

a cylindrical rotor;

a cylindrical stator with an eccentric, cylindrical, longitudinally extending bore, in which the rotor is mounted, the rotor and stator being concentric about a longitudinal axis, which is the axis of rotation of the rotor;

a plurality of unbiased vanes mounted in corresponding, substantially lengthwise-extending slots formed in the rotor, the unbiased vanes being substantially freely movable in their respective slots in a radial direction that is perpendicular to the axis of rotation;

an inlet port and an outlet port formed as openings through the stator;

in which:

an annular space between an outer surface of the rotor and an inner surface of the bore of the stator is uninterrupted;

compression and expansion chambers are formed between the rotor and the stator and are delimited by only the outer surface of the rotor, the inner surface of the stator, and respective pairs of the vanes.

* * * * *